US010293040B1

(12) United States Patent
Deisseroth

(10) Patent No.: US 10,293,040 B1
(45) Date of Patent: May 21, 2019

(54) **PHARMACEUTICAL COMPOSITIONS AND METHODS OF BLOCKING *BACILLUS ANTHRACIS***

(71) Applicant: MicroVAX, LLC, Manassas, VA (US)

(72) Inventor: Albert B. Deisseroth, Potomac, MD (US)

(73) Assignee: MICROVAX, LLC, Warrenton, VA (US)

( * ) Notice: Subject to any disclaimer, the term of this patent is extended or adjusted under 35 U.S.C. 154(b) by 0 days.

(21) Appl. No.: 14/695,445

(22) Filed: Apr. 24, 2015

Related U.S. Application Data

(63) Continuation-in-part of application No. 13/759,224, filed on Feb. 5, 2013, now abandoned, which is a continuation-in-part of application No. 11/593,458, filed on Nov. 6, 2006, now Pat. No. 9,533,036.

(60) Provisional application No. 61/599,969, filed on Feb. 17, 2012.

(51) Int. Cl.
| | | |
|---|---|---|
| *A61K 39/07* | (2006.01) | |
| *C07K 14/32* | (2006.01) | |
| *C07K 14/435* | (2006.01) | |
| *A61K 39/00* | (2006.01) | |

(52) U.S. Cl.
CPC .............. *A61K 39/07* (2013.01); *C07K 14/32* (2013.01); *C07K 14/435* (2013.01); *A61K 2039/5258* (2013.01); *A61K 2039/57* (2013.01); *A61K 2039/575* (2013.01); *C07K 2319/00* (2013.01); *C07K 2319/06* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 8,119,117 | B2* | 2/2012 | Deisseroth | C07K 14/005 424/199.1 |
| 8,236,295 | B1* | 8/2012 | Deisseroth | C07K 14/005 424/199.1 |
| 8,828,957 | B2* | 9/2014 | Deisseroth | A61K 39/0011 424/184.1 |
| 9,046,520 | B2* | 6/2015 | Semenova | A61K 39/07 |
| 9,102,742 | B2* | 8/2015 | Semenova | C07K 14/32 |
| 9,353,167 | B2* | 5/2016 | Deisseroth | A61K 39/0011 |
| 2004/0028695 | A1* | 2/2004 | Park | C07K 14/32 424/190.1 |
| 2007/0128223 | A1* | 6/2007 | Tang | A61K 39/145 424/209.1 |
| 2011/0286968 | A1* | 11/2011 | Kedl | A61K 39/12 424/85.6 |
| 2013/0149330 | A1* | 6/2013 | Deisseroth | A61K 39/07 424/192.1 |
| 2014/0080208 | A1* | 3/2014 | Deisseroth | C07K 14/005 435/320.1 |
| 2014/0234344 | A1* | 8/2014 | Banchereau | C07K 14/005 424/173.1 |
| 2016/0145590 | A1* | 5/2016 | Bachran | A61K 47/48261 424/94.67 |

OTHER PUBLICATIONS

Chitlaru et al, Immunological Reviews, 2010, 239:221-236.*
Brossier et al, Infection and Immunity, Feb. 2002, 70/2:661-664.*

* cited by examiner

*Primary Examiner* — Nita M. Minnifield
(74) *Attorney, Agent, or Firm* — Jacob Frank; Glenn Snyder

(57) ABSTRACT

The present invention is directed to pharmaceutical compositions and methods of inhibiting or blocking one or more virulence antigenic factors of *Bacillus anthracis*. Specifically, it involves the administering of an expression vector alone or in conjunction with a fusion protein. The expression vector has a transcription unit encoding a fusion protein composed of an antigenic factor of *Bacillus anthracis* attached through a linker to the aminoterminal end of the CD40 ligand. This fusion protein has the ability to generate antibodies which prevents *Bacillus anthracis* infection in an individual.

14 Claims, No Drawings

Specification includes a Sequence Listing.

```
                        SEQUENCE LISTING

<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Lys Thr Phe Ile Asp Phe Lys Lys Tyr Asn Asp Lys Leu Pro Leu Tyr
1               5                   10                  15

Ile Ser Asn Pro Asn
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

His Gly Asn Ala Glu Val His Ala Ser Phe Phe Asp Ile Gly Gly Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Tyr Ile Glu Pro Gln His Arg Asp Val Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Ser Pro Asp Thr Arg Ala Gly Tyr Leu Glu Asn Gly Lys Ile
1               5                   10
```

PHARMACEUTICAL COMPOSITIONS AND METHODS OF BLOCKING *BACILLUS ANTHRACIS*

CROSS-REFERENCE TO RELATED APPLICATIONS

This application is a continuation-in-part of U.S. patent application Ser. No. 13/759,224 filed Feb. 5, 2013, which in turn is a continuation-in-part of U.S. patent application Ser. No. 11/593,458, filed on Nov. 6, 2006, each of which applications, including all figures and tables, is incorporated herein by reference in its entirety.

This application also claims benefit under 35 U.S.C. § 119(e) of U.S. Provisional patent application Ser. No. 61/599,969, filed on Feb. 17, 2012, (via U.S. patent application Ser. No. 13/759,224 which claims priority to Provisional application 61/599,969), which, including all figures and tables, is incorporated herein by reference in its entirety.

FIELD OF THE INVENTION

The present invention relates generally to the field of antimicrobial prophylaxis. More specifically, it is directed to novel pharmaceutical compositions and methods of inhibiting or blocking one or more virulence antigenic factors of *Bacillus anthracis* infection via formulations containing fusion proteins derived from *Bacillus anthracis* fused to the CD40 ligand.

BACKGROUND OF THE INVENTION

The following discussion of the background of the invention is merely provided to aid the reader in understanding the invention and is not admitted to describe or constitute prior art to the present invention.

Overview of the Bacterium and Clinical Features of Anthrax:

The causative agent of anthrax is the spore-forming, relatively large (1.0-1.2×3-5 µm), Gram-positive *bacillus* named *Bacillus anthracis*. This bacterium is a major bioterrorism threat because its spores are extremely stable, are easily disseminated and are infectious via aerosol. The bacterium forms stable spores in unfavorable environments such as nutrient depletion. *B. anthracis* has a biphasic life cycle—it can exist as a metabolically inactive endospore or as a rapidly proliferating vegetative cell. The spores are in the range of 1 to 5 µm in diameter, an ideal size for inhalation into alveolar spaces. Once inside the host, the bacterium has both intracellular and extracellular stages of growth. The spores are taken up by macrophages into an acidified endosome, where they germinate and escape the antimicrobial environment.

Outbreaks of this zoonotic disease date back to antiquity and may have been responsible for the fifth and sixth plagues of Egypt described in the Bible. Today the disease is endemic among animals. Robert Koch first traced the complete life cycle of *B. anthracis* and showed that spores remain viable even in adverse environments. He cultured the *bacillus* in vitro and inoculated healthy animals that ultimately developed infection.

Anthrax is a serious disease that can affect both animals and humans. People can get anthrax from contact with infected animals, wool, meat, or hides. Anthrax is not known to spread from one person to another. Humans can become infected with anthrax by handling products from infected animals or by breathing in anthrax spores from infected animal products (like wool, for example). People also can become infected with gastrointestinal anthrax by eating undercooked meat from infected animals.

The clinical form of the disease is dependent upon the route of exposure and can manifest as cutaneous, gastrointestinal or inhalational anthrax:

(a) Cutaneous Anthrax: This is the most common form with close to 20% of these cases fatal if untreated. In this form, anthrax is a skin disease that causes skin ulcers and usually fever and fatigue.

(b) Gastrointestinal Anthrax: This form of the disease can result from eating raw/undercooked infected meat. Symptoms include fever, nausea, vomiting, sore throat, abdominal pain and swelling and swollen lymph glands. This form of the disease can lead to blood poisoning, shock and death.

(c) Inhalation Anthrax: This is a serious and often fatal form of anthrax that requires hospitalization. It occurs when the *bacillus* is inhaled. The initial symptoms may include a sore throat, mild fever and muscle aches. However, within days these symptoms are followed by severe breathing problems, shock, and often meningitis. This form of anthrax requires aggressive antibiotic treatment.

There are currently three known strains of *B. anthracis:*

(a) Ames Strain: This strain contains two virulence plasmids which separately encode for the three-protein toxin which mediates the lethal action of anthrax and a polyglutamic acid capsule which protects the anthrax bacteria from phagocytosis by neutrophils.

(b) Vollum Strain: This strain was initially isolated from a cow in Oxfordshire, UK in 1935. It was used by the British during World War II, and by both the US and UK during the 1960's. It is much more virulent than the Ames Strain. In 1951, Vollum 1B strain was isolated from a scientist who died at Fort Detrick Biological Warfare Center (operated by the US Army). Dr. William A Boyles, a 46 year old scientist, was accidentally exposed to this strain which is more virulent than the original Vollum Strain.

(c) Sterne Strain: This is an attenuated strain which contains the anthrax toxin but not the poly-glutamic acid capsule virulence plasmid.

Conventional Threat to the Civilian Population:

During the first half of the 20th century (up to and including World War II), anthrax has killed hundreds of thousands of animals and human beings in Asia, Australia, Africa, North America and Europe. Exposure to the dormant endospores of the bacterial organism (through the cutaneous, gastrointestinal or respiratory routes discussed above), can result in a fulminant rapidly progressive syndrome ending in septic shock and death in a matter of days. The endospores can produce infections for up to 100 years. Individuals at risk include those occupations which bring human beings into contact with the spores which contaminate animal hides or fur (woolsorters, drum makers), or individuals who eat the meat of infected animals (1).

Bioterrorist Threat to Civilian and Military Populations:

Anthrax also can be used as a weapon. This happened in the US in 2001 when anthrax was deliberately spread through the US postal system by sending letters with powder containing anthrax. This caused 22 cases of anthrax infection. According to a 1970 study by the WHO, the aerosolization of 50 kg of dried *B. anthracis* spores over a city with a population of 500,000 would incapacitate 125,000 people and kill 95,000, overwhelming medical resources and disrupting the infrastructure of most cities. As a result of programs designed to eradicate anthrax through animal vaccination, sterilization of animal products, only a few cases are now reported each year in the US. The major threat for exposure in the US is through biological warfare and terrorist activity (1).

Classic Examples of the Use of Anthrax in Biological Warfare and Terrorism:

As summarized below, the use of anthrax in biological warfare or as a weapon by terrorists can be catastrophic (1). The development of counter measures against this threat remains an unsolved problem until today (1). There are numerous examples of the use of anthrax endospores for biological warfare (1). Some are highlighted here:

1916: The German Army General Staff provided Swedish fighters with anthrax endospores for use in Finland against the Imperial Russian Army during World War I.

1930-1940: The Japanese Army tested the effect of direct administration of anthrax to human prisoners of war in Manchuria, killing thousands.

1942: The release of anthrax endospores on the Gruinard Island in Scotland by the British Biological Weapons testing program during World War II made that region uninhabitable until very recently.

1940-1945: During World War II, the British Royal Airforce was planning to drop on Germany up to 5 million cow cakes which had been impregnated with anthrax endospores.

1978: The Rhodesian Government used anthrax as a weapon in its war against black nationalists.

1979: Seven years after the USA and the USSR signed the Biological Weapons Convention, which provided for the destruction of all stores of biological weapons, an accidental release (the Sverdlovsk Accident) of anthrax endospores from a biological warfare production facility outside of Moscow killed 68 of the 94 individuals exposed.

2001: Attacks against government buildings in the USA (using envelopes which were loaded with anthrax endospores derived from the Ames strain and sent through the mail) occurred. The mortality was low due to the poor quality of the manufacturing process used.

Molecular Mechanism by which Anthrax Kills:

The anthrax bacterium has two virulence factors (1):

(1) A plasmid encoding poly-D-glutamic acid capsule protein which prevents phagocytosis by neutrophils;

(2) A plasmid which encodes the following three proteins which together constitute the anthrax Toxin: the protective antigen (PA), the edema factor (EF), and the lethal factor (LF).

The PA is non-toxic by itself, but the carboxyterminal end of this 83 kDa protein binds to two cellular receptors: the anthrax toxin receptor and the capillary morphogenesis protein 2 receptor. Neither LF nor EF is able to bind to or enter mammalian cells by themselves, but do so once bound to PA. EF is a calmodulin dependent adenylate cyclase. LF is a zinc dependent metalloprotease (1). The 83 kDa PA released by the anthrax bacterium binds to its cellular receptors. PA is then cleaved by a furin cellular protease into a 20 kDa fragment (at the N-terminus) and a 63 kDa fragment (at the C-terminus). The removal of the 20 kDa fragment reduces steric hindrance which otherwise prevents oligomerization of the PA into a heptameric ring-shaped structure. This heptameric structure can bind three molecules (any mixture of LF or EF) at nanomolar concentrations. This structure then relocates to detergent-resistant lipid microdomains in the plasma membrane where the heptamer of PA bound to EF and LF is internalized into the cell by endocytosis. Acidification within the endosome then allows the heptamer to insert itself into the endosomal membrane where it then translocates the EF and LF into the cytoplasm (1). LF then leads to cell death in host tissues and monocytes through inhibition of the MEK. LF has a zinc dependent metalloprotease action. This suppresses the function of neutrophils and monocytes. EF is a calmodulin dependent adenylate cyclase (1). The EF induced increase in adenylate cyclase may result in degranulation of monocytes (1). The complex formed between calmodulin and adenylate cyclase blocks calcium dependent signaling essential to the immune response. LF and EF target the endothelial cells that line vessels and serous cavities (pericardial cavity, pleural cavity and the peritoneal cavity), causing vascular leak, hypovolemic shock, septic shock, and cell death (1).

Previous Work on Vaccine Strategies for Anthrax:

Louis Pasteur produced the first veterinary live cell vaccine for anthrax in 1881, which comprised *B. anthracis* attenuated by passage at elevated incubation temperature. He tested the effect of the injection of anthrax into two groups of sheep, one group vaccinated 30 days earlier (two injections at 15 day intervals) and one not vaccinated with his vaccine. All the animals not vaccinated died and all of the animals in the vaccinated group lived (1).

The first human vaccine was introduced in 1954 (cell free). There are two types of vaccines currently available:

(a) Live-Attenuated Vaccine: This is called the Russian-Georgian vaccine (STI) which has been derived from the Stern Strain. This vaccine is not considered safe for use in any but the most fit human subjects due to the severity of the side effects.

(b) Cell Free Vaccine: An example is the USA vaccine (1) which is manufactured by Emergent BiSolutions (BioThrax) which is adsorbed onto aluminum hydroxide as adjuvant. This vaccine is approved by the US FDA for administration at 0, 2, and 4 weeks initially and then at 6, 12, and 18 months and yearly thereafter, for military personnel who are entering areas known to be endemic for anthrax. The week 2 dose was made optional in 2008. According to information on line in Google as part of the Anthrax Vaccine Immunization Program (AVIP), this vaccine is based on a fragment of the "protective antigen" (PA) which is described in the preceding section (1). This vaccine is designed to induce antibodies against the PA so as to neutralize the ability of the *Bacillus anthracis* to cause disease.

Shortcomings of Current Vaccine Strategies:

Some of the shortfalls of currently employed vaccines are discussed below.

Low Potency: As outlined above, there are three targets through which the lethality of the anthrax toxin could be blocked by neutralizing antibodies: the PA, the LF and the EF. The currently-employed USA vaccine, which is based on recombinant PA, appears to have a low potency and limited memory since it requires the use of an adjuvant and multiple boosting every 6 months×3 following induction and yearly thereafter (1). This vaccination schedule suggests that the vaccine itself is not very potent and requires constant boosting to maintain protection due to a weak memory response.

Toxicity: Press accounts of short and long term toxicities of this vaccine are available in the public domain. The side effects that have been associated with this vaccine (*Morbidity and Mortality Weekly Report* 59: page 11, 2009) include 10% serious adverse events (deaths, hospitalizations and permanent disability). In addition, short term adverse events have been observed at the injection site such as erythema, pain, itching and nodules. In addition, systemic symptoms such as fever, chills, myalgia, arthralgia and malaise are also associated with this vaccine.

Given the rise of virulent strains of *B. anthracis* which display antibiotic resistance, the goal of development of anthrax vaccines for high risk populations has emerged as an important priority. Unfortunately, this goal has not yet been realized. One factor that could prevent the success of vaccination is that the patients who are admitted to hospitals are often of advanced chronological age, are debilitated and/or are immunosuppressed as a result of chronic disease (4-7). These patients often do not respond to vaccination due to the diminished expression of CD40L in the CD40L helper T cells of these people (8-9). In this regard, another serious issue is that passive immunotherapy with opsonizing antibodies is unable to completely protect these individuals against anthrax.

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

Furthermore, all references, including publications, patent applications and patents, cited herein are incorporated by reference in full to the same extent as if each individual publication was specifically and individually indicated to be incorporated by reference. They are indicative of the levels of those of ordinary skill in the art to which the invention pertains and may be employed in the practice of the instant invention.

1. Definitions

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the terms "antigen" or "antigenic factors" refers broadly to any antigen to which a human, mammal, bird or other animal can generate an immune response. The terms "antigen" or "antigenic factors" as used herein refers broadly to a molecule that contains at least one antigenic determinant to which the immune response may be directed. The immune response may be cell-mediated, humoral or both. As is well known in the art, an antigen may be protein, carbohydrate, lipid, or nucleic acid or any combinations of these biomolecules. As is also well known in the art, an antigen may be native, recombinant or synthetic. For example, an antigen may include non-natural molecules such as polymers and the like. Antigens include both self antigens and non-self antigens. As used herein, "antigenic determinant" (or epitope) refers to a single antigenic site on an antigen or antigenic factor; it is a minimal portion of a molecule that recognized by the immune system, specifically by antibodies, B cells or T cells. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein is an amount that results in an increase in the immune response as measured by an increase in T cell activity or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [$Thr^1$]-MDP (Byersand Allison, *Vaccine* 5:223 (1987)), monophosphoryl lipid A (Johnson et al., *Rev. Infect. Dis.* 9:S512 (198)), and the like.

The term "vector" as used in this application contains a transcription unit (also known as an "expression vector"). It encompasses both viral and non-viral expression vectors that when administered in vivo can enter target cells and express an encoded protein. Viral vectors have evolved means to overcome cellular barriers and immune defense mechanisms. Viral vectors suitable for in vivo delivery and expression of an exogenous protein are well known in the art and include adenoviral vectors, adeno-associated viral vectors, retroviral vectors, vaccinia vectors, pox vectors, herpes simplex viral vectors, etc. Viral vectors are preferably made replication defective in normal cells. For example, see U.S. Pat. Nos. 6,669,942; 6,566,128; 6,794,188; 6,110, 744; 6,133,029. On the other hand, nonviral gene carriers consistently exhibit significantly reduced transfection efficiency as they are hindered by numerous extra- and intracellular obstacles. Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture is useful as a vehicle for non-viral expression vectors. See U.S. Pat. No. 6,147,055. Polycation-DNA complexes also may be used as a nonviral gene delivery vehicle. See Thomas et al., *Appl Microbiol Biotechnol* (2003) 62(1):27-34. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (also known as "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous tumor antigen signal sequence also may be used to direct secretion.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that block *B. anthracis*. The term "opsonizing antibody" as used herein refers to antibodies that bind to one or more receptors on *B. anthracis* and "mark" it for subsequent ingestion, blocking or inhibition via phagocytes such as macrophages. In this context, an opsonizing antibody attaches to one or more *B. anthracis* antigenic factors and acts as a binding enhancer for phagocytosis.

The term "linker" as used employed in this application with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See, e.g. Arai et al. *Protein Engineering*, Vol. 4, No. 8, 529-532, August 2001). In certain embodiments of the present invention, the linker is from about 3 to about 15 amino acids long, more preferably from about 5 to about 10 amino acids long. However, longer or shorter linkers may be used or the linker may be dispensed with entirely. Longer linkers may be up to about 50 amino acids, or up to about 100 amino acids. One example of a linker well-known in the art is a 15 amino acid linker consisting of three repeats of four glycines and a serine (i.e., [$Gly_4Ser_3$)].

2. List of Abbreviations

Some of the abbreviations used in the instant specification are listed below:
Ad—adenoviral
Sig—signal sequence
TAA—target associated antigen
ET—epitopic target
ecd—extracellular domain
SC—subcutaneous or subcutaneously
CD40L—CD40 ligand
CMV—cytomegalovirus
PA—protective antigen
EF—edema factor
LF—lethal factor 3. Background on Poor Response to Vaccine Among Older Individuals In general, the response to vaccination may be limited by several factors: (a) low immunogenicity of the target antigen; (b) the state of health and the age of the individual; (c) chronic infections or cancer; or (d) other host factors which lead to defective function of CD8 T cells, CD4 T cells, B cells and dendritic cells. The instant inventor (10-18) has discovered that the linkage of the target antigen or a piece of the target antigen to the extracellular domain (ecd) of the CD40L at its aminoterminal end results in a dramatic increase in the magnitude of the immune response to the vaccine in young as well as older test subjects. This strategy converts weak antigens into strong and potent immunogens, and also overcomes states of anergy due to central or peripheral tolerance. This is due to the fact that the engagement of the CD40 receptor on antigen-specific B and CD8 T cells by the carboxyl terminal end of the CD40L on the surface of CD4 helper T cells is an essential step for these cells to expand in number in response to vaccination (8-9). For example, in older individuals, the absence of the presentation of the CD40L on activated CD4 helper T cells reduces the magnitude of the immune response to influenza vaccination. Recent analyses of human influenza vaccination clinical data show that less than 20% of individuals above 55 years of age develop a fully protective neutralizing antibody response to the yearly multivalent particle inactivated human influenza vaccine (4-7). This is due to the acquisition of both quantitative as well as qualitative defects such as loss of expression of CD40 ligand (CD40L) on CD4 helper T cells during activation (8-9) in the immune response as individuals reach the $5^{th}$ and $6^{th}$ decades of life. The inventor's TAA/ecdCD40L vaccine strategy (discussed next) overcomes this obstacle.

4. TAA/ecdCD40L Vaccine Platform

As discussed above, not only is a lack of potency and a limited memory response doom the success of any vaccine (including anthrax vaccine), but a vaccine will be unsuccessful if individuals being vaccinated are of advanced chronological age, are debilitated, are immunosuppressed by the presence of chronic disease (4-7), or do not respond well to vaccination due to the diminished expression of CD40L in the CD40L helper T cells of these people (8-9). The presence of the CD40L on CD4 helper T cells is necessary for the expansion of antigen specific T cells and B cells as a result of vaccination.

In order to overcome these problems, the inventor's laboratory (10-18) developed a TAA/ecdCD40L (TAA-target associated antigen) vaccine platform that is specifically designed to overcome the defective response to vaccination in immunosuppressed, debilitated patients who are of advanced chronological age. The basis for the success of this vaccine is that it supplies a potent immunostimulatory signal (ecdCD40L) that is missing in older people and thought to be one of the reasons for the diminished response of older individuals to vaccination (8-9). This vaccination is customarily given subcutaneously (SC) either as a TAA/ecdCD40L protein or as an Ad-sig-TAA/ecdCD40L vector prime-TAA/ecdCD40L protein boost (10-18).

One of the reasons for the success of this platform is that it supplies a potent immunostimulatory signal (ecdCD40L) that is missing in older people. The presence of the TAA/ecdCD40L (i) activates the DCs, (ii) activates the antigen specific B cells and T cells, (iii) increases the potency of the vaccine, and (iv) directs the TAA along a Class I as well as a Class II MHC presentation pathway within the DC (8-9). This vaccination can be given subcutaneously as a TAA/ecdCD40L protein, as a subcutaneous injection of the Ad-sig-TAA/ecdCD40L vector, as an intramuscular injection of a DNA plasmid expression vector encoding the TAA/ecdCD40L protein, or as a subcutaneous injection of the fusion protein itself (10-18).

In order to generate a vaccine that can dramatically increase the potency of the immune response in healthy subjects, as well as subjects in whom the function of CD4 helper T cells is defective and thereby circumvent the functional defects in the immune response that are acquired in such individuals, as well as increase the immunogenicity of weak antigens, such as those present in Anthrax, the inventor's laboratory (10-18) designed the TAA/ecdCD40L vaccine strategy.

There are several versions of this vaccine: (1) a first version, the TAA/ecdCD40L transcription unit is embedded in a replication incompetent adenoviral vector (Ad-sig-TAA/ecdCD40L) which is used as an initial priming injection, followed by two SC injections of the TAA/ecdCD40L protein, and (2) a second version, where the vaccine consists solely of the TAA/ecdCD40L fusion protein. The TAA is connected through a linker to the amino-terminus of the extracellular domain (ecd) of the potent immunostimulatory signal CD40 ligand (CD40L). The attachment of the TAA to the CD40L accomplishes two things: (1) the binding of the TAA/ecdCD40L protein to the CD40 receptor on the dendritic cells (DCs) as well as on the B cells and T cells, activates these cells by replacing the CD40L signal which is missing on the plasma membrane of the CD4 helper T cells of older individuals (8-9); and (2) once the TAA/ecdCD40L protein is engaged on the CD40 receptor of the DC, the entire TAA/ecdCD40L protein is internalized into the DC in a way that allows the TAA to be processed through the Class I as well as the Class II MHC presentation pathways (10-18).

The activated TAA loaded DC then migrate to the regional lymph nodes (11) where they can activate and induce expansion of the TAA specific CD8 effector T cells. These antigen specific CD8 effector cells become increased in number in the lymph nodes (10-11, 13), following which they egress from the lymph nodes into the peripheral blood. The antigen specific CD8 effector T cells then exit the intravascular compartment and enter into the extravascular sites of inflammation or infection (13). In addition to showing that this vaccine increases the antigen specific CD8 effector T cells in the sites of inflammation, the inventor's laboratory have shown that the activation and expansion of the B cells by the TAA/ecdCD40L protein increases the levels of the TAA specific antibodies in the serum (10-18).

5. Innovative Approach for a *Bacillus Anthracis* Vaccine—the PA/ecdCD40L and the LF/ecdCD40L Vaccines After reviewing the design features of all existing anthrax vaccines and carefully evaluating multiple functions of the Anthrax Lethal Toxin, the inventor designed a novel anthrax vaccine strategy which may be virtually universal in nature. More specifically, the inventor has create an improvement over the existing Anthrax vaccines by creating four different Anthrax vaccines, each directed to a separate individual function of the Anthrax Lethal Toxin:
 1. PA domains which bind to cellular receptors;
 2. PA peptides which have been shown to be essential for the translocation of the LF and the EF from the endosome into the cytosol;
 3. LF peptides which bind to PA;
 4. LF peptides which are involved in the lethal enzymatic activity of anthrax: ADP-ribotransferase.

By linking peptides from each of these functions to the ecdCD40L, it is believed that the immunogenicity of each of these peptides is enhanced. By inducing an immune response against four separate functions, the probability of acquisition of mutational change by the anthrax bacterial population is reduced to an astronomically low number.

Vaccine #1—PA Domains which Bind to Cellular Receptors:

The first vaccine is constructed by taking a fragment of the PA in the region of Asparagine 682 which is embedded in the domain of PA (AA 673-693) which binds to its cellular receptors (2-3). Mutational change of this amino acid (Asparagine 682) and other neighboring amino acids in this region have been shown to block binding of PA to its cellular receptors, which is essential for anthrax to kill cells (2-3). A 20 amino acid fragment from this region of PA (AA=KTFIDFKKYNDKLPLYISNPN-SEQ ID NO. 1) will be attached to the N terminus of the ecd of CD40L to make the vaccine. Asparagine 682 (N in the sequence KKYNDKL in the middle of SEQ ID NO. 1 shown above), is in the middle of SEQ ID NO. 1. This 20 amino acid region of PA has been shown to be important for the interaction and binding of PA to its cellular receptors which is necessary for infection of cells by anthrax. This vaccine will be designated as follows: Ad-sig-PA$_{682}$/ecdCD40L vector prime and PA$_{682}$/ecdCD40L protein boost;

The cDNA for a PA fragment encoding the epitope target described above will be attached via a cDNA encoding an 8 amino acid linker to a third cDNA at the amino terminus of the extracellular domain (ecd) of the CD40L. This cDNA, encoding a secretable PA/ecdCD40L protein, will be inserted into the Ad-sig-PA/ecdCD40L vector or a plasmid expression system encoding a PA/ecdCD40L protein.

The ability to protect mice from lethal challenges of anthrax will be tested at varying doses of anthrax in permissive mouse strains (DBA/J) by vaccination: SC injection with the PA$_{682}$/ecdCD40L protein alone, the cDNA for the PA$_{682}$/ecdCD40L, and the Ad-sig-PA$_{682}$/ecdCD40L vector prime (V) PA$_{682}$/ecdCD40L protein boost in a VPP schedule (see above).

Vaccine #2—PA Peptides which have been Shown to be Essential for the Translocation of the LF and the EF from the Endo Some into the Cytosol:

A peptide containing amino acids 305-319, will be taken from the "loop neutralizing determinant" or LND of domain #2 of PA (LNDPA). This region has been shown to be essential for the translocation of EF and LF into the cytosol when these two toxic factors bind to PA (19-21). The sequence of this domain is in single letter amino acid code: HGNAEVHASFFDIGGS (SEQ ID NO. 2). Vaccination with this peptide has been shown to protect mice (19). This fragment will be attached via a cDNA encoding an 8 amino acid linker to the amino-terminus of the extracellular domain (ecd) of the CD40L. This PA/ecdCD40L cDNA encoding a secretable PA/ecdCD40L protein will be inserted into the Ad-sig-PA/ecdCD40L vector or a plasmid expression system encoding a PA/ecdCD40L protein.

Software will be used for the selection of a peptide from this region which is recognized by both Class I and II MHC and which can induce PA specific cytotoxic T cells and neutralizing antibodies. In addition, the size of the PA fragment used for the vaccination will be limited such that the introduction of the PA fragment into a fusion protein attached to the N-terminus of the ecd of the CD40L will not destabilize the conformation of the C-terminal end of the CD40L such that it can still bind to the CD40 receptor on Dendritic Cells (DCs).

The ability to protect mice from lethal challenges of anthrax will be tested at varying doses of anthrax in permissive mouse strains (DBA/J) by vaccination (SC injection) with the $PA_{305}$/ecdCD40L protein alone, the cDNA for the $PA_{305}$/ecdCD40L, and the Ad-sig-$PA_{305}$/ecdCD40L vector prime (V) $PA_{305}$/ecdCD40L protein boost in a VPP schedule (see above).

Vaccine #3—LF Peptides which Bind to PA:

A peptide will be chosen in the region of AA 257-266 which is in the domain of the Lethal Factor (LF) (AA=YIEPQHRDVL-SEQ ID NO. 3) which binds to PA, and has been shown to be a target of neutralizing antibodies, has been chosen (22). Antibodies which bind this peptide protect 50% of A/J mice against a 3×LD lethal challenge of lethal toxin (22). The candidate peptide will be screened using software for the selection of a peptide from this region which is recognized by both Class I and II MHC and which can induce PA specific cytotoxic T cells and neutralizing antibodies. In addition, the size of the PA fragment used for the vaccination will be limited such that the introduction of the PA fragment into a fusion protein attached to the N-terminus of the ecd of the CD40L will not destabilize the conformation of the C-terminal end of the CD40L such that it can still bind to the CD40 receptor on Dendritic Cells (DCs).

Vaccine #4—LF Peptides which are Part of the ADP-Ribotransferase Like Domain:

A peptide in the region of AA 539-552 of the LF (AA=SPDTRAGYLENGKI—SEQ ID NO. 4) which contains the ADP-ribotransferase-like domain of LF has been chosen (22). Antibodies which bind this peptide protect 60% of A/J mice against a $3\times LD_{50}$ lethal challenge of lethal toxin (22).

Fragment/Peptide Selection:

Although it is believed that the specific fragment/peptide selections suggested in the above described Vaccines #1 through #4, are choices that might result in an effective overall vaccine, any one or more of the fragment/peptide selections noted above may be substituted for, by a fragment/peptide having at least similar, if not more effective, binding characteristics. In addition, the use of four different peptides each attached to ecdCD40L to produce 4 independent vaccines will reduce the probability of immunological escape.

Method of Construction of Vaccines #3 and #4:

A cDNA for each of these peptides will be attached via a cDNA encoding an 8 amino acid linker to the amino-terminus of the extracellular domain (ecd) of the CD40L. Each of these cDNAs, encoding one of the above described secretable LF/ecdCD40L proteins, will be inserted into the Ad-sig-LF/ecdCD40L vector or a plasmid expression system encoding a LF/ecdCD40L protein.

The ability to protect mice from lethal challenges of anthrax will be tested at varying doses of anthrax in permissive mouse strains (DBA/J) by vaccination (SC injection) with the LF/ecdCD40L protein alone, the cDNA for the LF/ecdCD40L, and the Ad-sig-LF/ecdCD40L vector prime (V) LF/ecdCD40L protein boost in a VPP schedule (see above).

These vaccines will be designated as follows:
a. $LF_{257}$/ecdCD40L
b. $LF_{539}$/ecdCD40L Antibody Solutions:

Although the above description is specific to anthrax vaccine solution, it is also understood that the above concept can be applied to a "passive immunization strategy by generating therapeutic antibodies to each of these targets through the use of the PALF/ecdCD40L platform described above.

Advantages of the Ad-Sig-PA or LF/ecdCD40L Vector Prime-P or LF/ecdCD40L Protein Boost:

This novel vaccine strategy will convert a weakly immunogenic peptide targets which induce weak memory response from anthrax into potent immunogens which induce an immune response vaccination with memory for at least a year. The use of four of these vaccines together, because they are targeted to essential function of the lethal toxin of anthrax, will reduce the probability that the Anthrax population can escape the negative selection of the immune response. This vaccine will be applicable for use population wide in the USA as well as for the military personnel. Moreover, this vaccine will be applicable to individuals with conditions in the subjects to be vaccinated that have diminished the helper function of CD4 T cells that depend on the expression of CD40L. The four vaccines listed above will attack 4 different functional regions of the Anthrax Toxin all of which have been shown to induce neutralizing antibodies:

a. The PA receptor binding domain in the region of Asparagine 682 (AA=673-693-SEQ ID NO. 1), which is in the receptor binding domain;
b. The PA region (AA=305-319-SEQ ID NO. 2) that is necessary for the translocation of the LF and EF to the cytosol of the target cells;
c. The AA 257 region of LF (AA=257-266-SEQ ID NO. 3) that is necessary for the binding of LF to PA, and
d. The AA 539 region of LF (AA=539-552-SEQ ID NO. 4) that contains the adenyl cyclase enzymatic functional domain of LF.

All of the target regions have been shown to induce neutralizing antibodies. By combining all four vaccines into one, and attaching each one to ecdCD40L, the potency of the anthrax vaccine will be increased dramatically, the ability to induce memory will be enhanced, and the ability to prevent breakthrough of Anthrax due to mutagenic escape will be prevented.

Advantages of the Multivalent PALF/ecdCD40L Anthrax Vaccine:

This vaccine will provide an immunization procedure that in contradistinction to the available vaccine for anthrax in the USA:

a. Induces a strong memory response
b. Induces a potent immune response
c. Overcomes the potential problems with vaccination outlined above that apply to the existing Anthrax vaccine in the USA, and is useful for populations of test subjects that have reduced responsiveness to vaccination due to advanced chronological age and/or anergy arising from chronic disease.
d. Non-toxic since the amount of target antigen required to induce an immune response will be much lower and involve fewer injections (administrations) over a much shorter period of time than is the case with the current vaccine in the USA.

The PALF/ecdCD40L Vaccine:

In accordance with one embodiment, a vaccine against anthrax that is comprised of PA/ecdCD40L and LF/ecdCD40L fusion proteins which will be generated by attaching a fragment from the anthrax toxin proteins to the N-ter of the ecd of the CD40L in such a way that the vaccine induces a potent humoral and cellular immune response to four separate toxin functions which contain the following antigens:

a. The PA receptor binding domain in the region of Asparagine 682 (AA=673-693-SEQ ID NO. 1), which is in the receptor binding domain;
b. The PA region (AA=305-319-SEQ ID NO. 2) that is necessary for the translocation of the LF and EF to the cytosol of the target cells;
c. The AA 257 region of LF (AA=257-266-SEQ ID NO. 3) that is necessary for the binding of LF to PA, and
d. The AA 539 region of LF (AA=539-552-SEQ ID NO. 4) that contains the adenyl cyclase enzymatic functional domain of LF.

In this embodiment, the use of a combination of the four vaccines proposed above will attack 4 different functional regions of the Anthrax Toxin all of which have been shown to induce neutralizing antibodies. The tetradentate nature of this vaccine will reduce the probability of the anthrax population escaping the negative selection of the vaccine. In addition, this embodiment may convert a weakly immunogenic, weakly potent vaccination with limited memory into a potent vaccine with a durable memory response that is applicable for use population wide in the USA. Moreover, this vaccine will be applicable to individuals with conditions that have diminished the helper function of CD4 T cells that depend on the expression of CD40L.

6. References Cited

1. Anthrax-Wikipedia, http://en.wikipedia.org/wiki/Anthrax.
2. Varughese M, Teixeira A V, SLiu S, and Leppla S H. Identification of a receptor binding region within domain 4 of the Protective Antigen component of Anthrax Toxin. Infection and Immunity 67: 1860-1865, 1999.
3. Bradley K A, Mogridge J, Morez M, Collier R J, and Young J A T. Identification of the cellular receptor for anthrax toxin. Nature 414: 225-229, 2001.
4. Jefferson T, Rivetti D, Rivetti A, Rdin M, Di Pietrantonj C, and Demicheli V. Efficacy and effectiveness of influenza vaccines in elderly people: a systematic review. Lancet 366, 1165-1174, 2005.
5. Goodwin K, Viboud C, and Simonsen L. Antibody response to influenza vaccination in the elderly: a quantitative review. Vaccine 24, 1159-1169, 2006.
6. Simonsen L et al., Lancet Inf. Dis 7: 658-666, 2007.
7. Jackson M L et al., Lancet 372: 398-405, 2008.
8. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. Journal of General Virology 84, 1623-1628, 2003.
9. Eaton S M et al., J. Exp. Med. 200: 1613-1622, 2004.
10. Zhang L, Tang Y, and Deisseroth A: Adenoviral vectors encoding a secretable HPV 16 E7/CD40 ligand fusion protein induce immunity for up to one year in a murine model. PNAS, 100: 15101-15106, 2003.
11. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. Blood, 104: 2704-2713, 2004.
12. Akubulut H, Tang Y C, Maynard J, and Deisseroth A. Dendritic cells improve the efficacy of vector targeted chemotherapy in breast cancer. Molecular Cancer Therapeutics 5: 1975-1985, 2006.
13. Tang, Y C, Maynard J, Akbulut H, Fang X M, Zhang W W, Xia X Q, Koziol J, Linton P J, and Deisseroth. Vector Prime/Protein Boost Vaccine Which Overcomes Defects Acquired During Aging and Cancer. J. Immunology, 177: 5697-5707, 2006.
14. Tang Y, Akbulut H, Maynard J, Zhang L, Petersen L, and Deisseroth A. Vaccine strategies for cancer and infectious diseases in the elderly. Gene Therapy 2007, Edited by T. Ochiai, H. Shimada, and M. Tagawa, Chiba, Japan, pp. 78-85, 2007.
15. Akbulut H, Tang Y C, Maynard J, and Deisseroth A. Chemotherapy targeted to cancer tissue potentiates antigen specific immune response induced by vaccine for antigen loading and activation of dendritic cells. Molecular Therapy, 10: 1753-1760, 2008.
16. Tang, Y C, Linton, P J, Thoman M, and Deisseroth A. Symposium in Writing: Vaccine for Infections and Cancer. Cancer Immunology Immunotherapy 58: 1949-1957, 2009.
17. Han T H, Park Y H, Maynard J, Li P C, Tang Y C, and Deisseroth A. Ad-sig-BcrAbl/ecdCD40L Vector Prime-BcrAbl/ecdCD40L Protein Boost Vaccine for P210Bcr-Abl Protein, Bone Marrow Transplantation, 45: 550-557, 2010.
18. Akbulut H, Tang Y C, Akbulut G, Maynard J, and Deisseroth A. Vaccine combined with vector targeted chemotherapy reduces levels of cancer stem cells and improves outcome of cancer treatment, Gene Therapy 17: 1333-1340, 2010.
19. Oscherwitz J, Yu F, and Cease K B. A synthetic peptide vaccine directed against the 2 beta2-2beta3 loop of domain 2 of protective antigen protects rabbits from inhalation Anthrax. Journal of Immunology 185: 3361-3368, 2010.
20. Singh Y, Klimpel K R, Arora N, Sharma M, and Leppla S H. The chymotrysin-sensitive site, FFD315, in anthrax toxin protective antigen is required for translocation of lethal factor. J. Biol. Chem. 269: 29039-29046, 1994.
21. Singh Y, Kanna H, Chopra A P, and Mehra V. A dominant negative mutant of Bacillus anthracis protective antigen inhibits anthrax toxin action in vivo. J. Biol. Chem. 276: 22090-22094, 2001.

22. Crowe S R, Garman L, Engler R J M, Farris A D, Ballard J D, Harley J B, and James J A. Anthrax vaccination induced anti-lethal factor IgG: fine specificity and neutralizing capacity. *Vaccine* 29: 3670-3678, 2011.

I claim:

1. A composition, including at least four sub-compositions, for inhibiting the entry of toxic virulence antigenic factors of *Bacillus anthracis* in normal cells of an individual by generating antibodies for blocking the binding of the protective antigen protein (PA) to receptors on mammalian cells, and to the edema factor (EF) enzyme, and blocking the lethal enzymatic activity of the lethal factor (LF), the composition comprising:
   (i) an expression vector carrying transcription units encoding each of said four sub-compositions, each of said four sub-compositions consisting of (a) a peptide fragment target directed to at least one functional region of said virulence antigenic factors that is distinct from functional regions in each of the other three peptide fragment targets, said peptide fragment targets comprising SEQ ID NO. 1/ecdCD40L, SEQ ID NO. 2/ecdCD40L, SEQ ID NO. 3/ecdCD40L, and SEQ ID NO. 4/ecdCD40L, and (b) each of said sequence identification numbers (SEQ ID NOS.1-4) connected to an amino terminus of an extracellular domain (ecd) of a CD40 ligand to form four distinct secretable fusion proteins, and wherein each of said sub-compositions generates neutralizing antibodies against said *Bacillus anthracis* toxic virulence antigenic factors, and
   (ii) one or more adjuvants.

2. The composition of claim 1, wherein said antigenic factor and ecdCD40 ligand are covalently linked.

3. The composition of claim 1, wherein said ecdCD40 ligand is human ecdCD40 ligand.

4. The composition of claim 2, wherein the transcription unit additionally encodes a linker between said antigenic factor and the aminoterminal end of ecdCD40 ligand.

5. The composition of claim 1, wherein the transcription unit encodes a secretory signal sequence.

6. The composition of claim 1, wherein said expression vector is a plasmid DNA or viral vector.

7. The composition of claim 1, wherein said viral vector is an adenoviral vector.

8. A method of blocking *Bacillus anthracis* infection or suppression virulence of *Bacillus anthracis* in an individual in need thereof, comprising administering to the individual an effective amount of the composition of claim 1.

9. The method of claim 8, wherein said method further comprises additionally administering an effective amount of solely said fusion protein proteins each comprising a *Bacillus anthracis* antigenic factor and ecdCD40 ligand.

10. The method of claim 8, wherein said method is a passive immunization regimen that involves blocking of the progression of multiple strains of *Bacillus anthracis* or suppressing virulence of multiple strains of *Bacillus anthracis*.

11. The method of claim 8, wherein the individual is debilitated, immunosuppressed or of advanced chronological age.

12. The method of claim 8, wherein said fusion proteins have the ability to generate Class I and Class II MEW cytotoxic T cells.

13. The method of claim 9, wherein solely said fusion proteins are administered following administration of the composition of claim 1.

14. The method of claim 9, wherein following administration of said composition of claim 1, solely said fusion proteins are subcutaneously administered as a single dose or as multiple doses as part of a passive immunization regimen.

* * * * *